United States Patent
Aizawa et al.

(10) Patent No.: US 10,295,470 B2
(45) Date of Patent: May 21, 2019

(54) MICROSPECTROSCOPE

(71) Applicant: JASCO Corporation, Tokyo (JP)

(72) Inventors: Kento Aizawa, Tokyo (JP); Tsutomu Inoue, Tokyo (JP); Masateru Usuki, Tokyo (JP)

(73) Assignee: JASCO Corporation, Tokyo (JP)

( * ) Notice: Subject to any disclaimer, the term of this patent is extended or adjusted under 35 U.S.C. 154(b) by 0 days.

(21) Appl. No.: 15/560,256

(22) PCT Filed: Mar. 22, 2016

(86) PCT No.: PCT/JP2016/058889
§ 371 (c)(1),
(2) Date: Sep. 21, 2017

(87) PCT Pub. No.: WO2016/152823
PCT Pub. Date: Sep. 29, 2016

(65) Prior Publication Data
US 2018/0067053 A1 Mar. 8, 2018

(30) Foreign Application Priority Data
Mar. 25, 2015 (JP) ................. 2015-062307

(51) Int. Cl.
*G01N 21/65* (2006.01)
*G01J 3/08* (2006.01)
(Continued)

(52) U.S. Cl.
CPC .............. *G01N 21/65* (2013.01); *G01J 3/027* (2013.01); *G01J 3/0208* (2013.01); *G01J 3/06* (2013.01);
(Continued)

(58) Field of Classification Search
CPC ....... G01N 21/65; G01N 21/6458; G01J 3/08; G01J 3/44
See application file for complete search history.

(56) References Cited

U.S. PATENT DOCUMENTS 8,923,568 B2 * 12/2014 Olson .................. G01N 21/274
348/79
9,383,569 B2 * 7/2016 Kang .................... G02B 21/244
(Continued)

FOREIGN PATENT DOCUMENTS

JP 972848 3/1997
JP 2007179002 A2 7/2007
(Continued)

OTHER PUBLICATIONS

International Search Report dated Apr. 19, 2016 filed in PCT/JP2016/058889.
(Continued)

*Primary Examiner* — Kara E. Geisel
*Assistant Examiner* — Maurice C Smith
(74) *Attorney, Agent, or Firm* — Rankin, Hill & Clark LLP

(57) ABSTRACT

To provide a microspectroscope that can perform a wide range mapping measurement with high sensitivity, at high speed, and with high wavelength resolution.
The Raman spectroscope comprises: a unit for linearly irradiating excitation light; a movable stage for a sample; an objective lens for focusing Raman light from the linear irradiation region; an incident slit provided at the imaging position of Raman light; a spectrometer for diffusing the passing light; a CCD detector for detecting Raman spectral image; and a control device for controlling the mapping measurement by synchronizing the movable stage and the CCD detector. The control device controls the movable stage to move in the direction orthogonal to the longitudinal
(Continued)

direction of the linear irradiation light and obtain one average spectrum. At the same time, the control device is configured to perform the cycle of the CCD detector while the stage is moving to obtain one average spectrum of the moving region of the linear irradiation region in one light detection cycle.

10 Claims, 11 Drawing Sheets

(51) Int. Cl.
*G01J 3/44* (2006.01)
*G02B 21/00* (2006.01)
*G01J 3/06* (2006.01)
*G01J 3/28* (2006.01)
*G01J 3/02* (2006.01)
*G01J 3/10* (2006.01)
*G01N 21/64* (2006.01)
*G01N 21/59* (2006.01)

(52) U.S. Cl.
CPC .............. *G01J 3/08* (2013.01); *G01J 3/2823* (2013.01); *G01J 3/44* (2013.01); *G02B 21/0036* (2013.01); *G02B 21/0064* (2013.01); *G01J 3/0256* (2013.01); *G01J 3/10* (2013.01); *G01J 3/2803* (2013.01); *G01N 21/6458* (2013.01); *G01N 2021/5957* (2013.01)

(56) References Cited

U.S. PATENT DOCUMENTS

| | | | |
|---|---|---|---|
| 9,588,328 B2* | 3/2017 | Kalkbrenner | G01N 21/6408 |
| 2007/0132994 A1 | 6/2007 | Kobayashi et al. | |
| 2012/0257037 A1 | 10/2012 | Raicu et al. | |
| 2013/0050782 A1 | 2/2013 | Heng | |
| 2014/0002819 A1 | 1/2014 | Kobayashi | |
| 2014/0313313 A1 | 10/2014 | Soenksen | |
| 2014/0333755 A1* | 11/2014 | Adams | G01N 21/85 |
| | | | 348/86 |
| 2015/0009361 A1* | 1/2015 | Liu | H04N 5/2352 |
| | | | 348/229.1 |
| 2016/0006918 A1* | 1/2016 | Lindau | H04N 5/372 |
| | | | 348/231.5 |

FOREIGN PATENT DOCUMENTS

| | | |
|---|---|---|
| JP | 2012189891 A2 | 10/2012 |
| JP | 201448088 | 3/2014 |
| JP | 2014507662 | 3/2014 |
| WO | 2006028439 A1 | 3/2006 |
| WO | 2009093050 A1 | 7/2009 |

OTHER PUBLICATIONS

Extended European Search Report dated Nov. 26, 2018 issued in the corresponding European patent application No. 16768726.8.

* cited by examiner

FIG.2
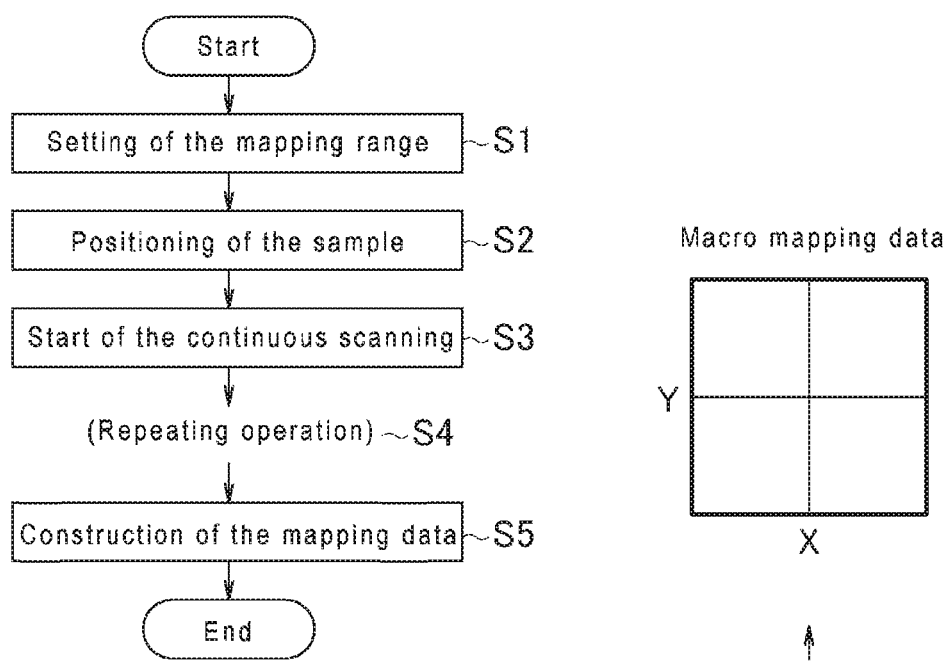
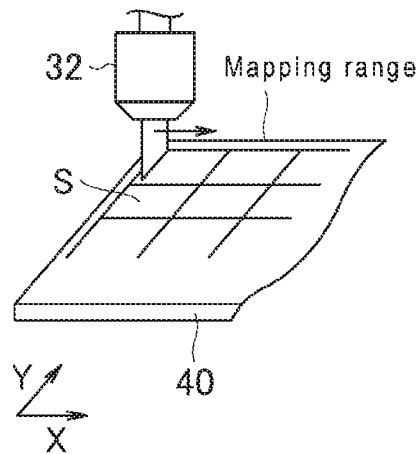
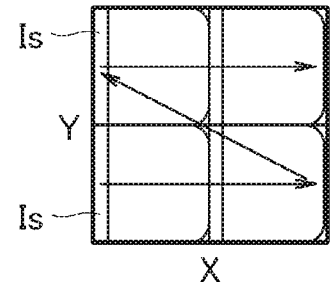

FIG.6

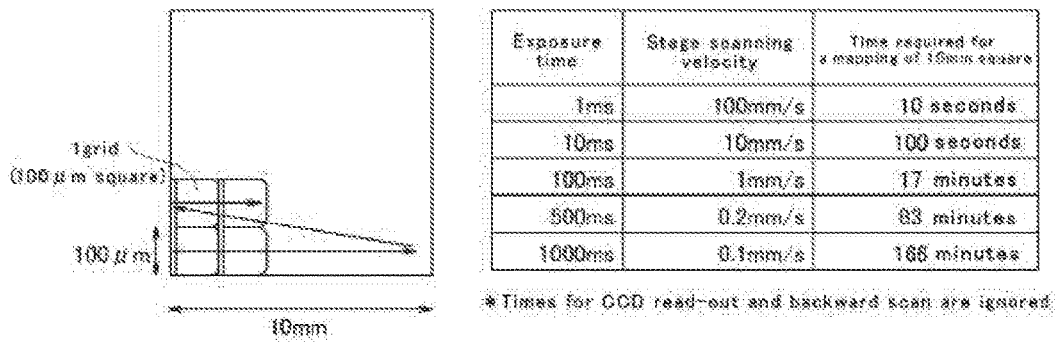

FIG.7

|  | 1 μm Step | 5 μm Step | 10 μm Step | 100 μm Step |
|---|---|---|---|---|
| Measurement points (□10mm region) | 100,000,000 | 4,000,000 | 1,000,000 | 10,000 |
| Time 1ms/point | 28 hours | 67 minutes | 17 minutes | 10 seconds |
| 5ms/point | 6 days | 5.5 hours | 83 minutes | 50 seconds |
| 10ms/point | 12 days | 11 hours | 2.8 hours | 100 seconds |
| 50ms/point | 58 days | 55 hours | 14 hours | 500 seconds |
| 100ms/point | 116 days | 4.6 days | 28 hours | 17 minutes |
| 500ms/point | 579 days | 23 days | 6 days | 83 minutes |
| 1000ms/point | 1157 days | 46 days | 12 days | 2.8 hours |

Great number of measurement points, low sensitivity

Practical setting measurement Points, sensitivity

Comparative example of the macro irradiation

MICROSPECTROSCOPE

RELATED APPLICATIONS

This application claims the priority of Japanese Patent Application No. 2015-062307 filed on Mar. 25, 2015, the disclosure of which is incorporated herein by reference in its entirety.

FIELD OF THE INVENTION

The present invention relates to improvements in a microspectroscope for performing a two- or three-dimensional mapping measurement regarding to a component, physical property, shape and the like of a sample by obtaining spectra of a reflected light, a transmitted light, an emitted light or a scattered light from a plurality of positions within a measurement region of the sample. For example, a Raman spectroscope, a fluorescence spectroscope, an infra-red spectroscope and the like for performing an area analysis to a measurement region of a sample are included in the scope of application.

BACKGROUND OF THE INVENTION

Conventionally, laser microspectroscopes of confocal optical systems that are suitable for a point analysis of a sample is known. This device irradiates a laser light onto a micro region of a sample at pinpoint and forms a beam spot having a diameter size of approximately 1 μm. Then, it obtains spectra of the light from the point with high spatial resolution. Specifically, an objective lens, an imaging lens and a single aperture are used to focus the light from the sample with the objective lens and form its image by the imaging lens, and the opening of the single aperture is positioned at an imaging position. At this point, the light other than the light from the focus of the objective lens is blocked. Therefore, a point analysis with high spatial resolution is possible by spectrally separating the passing light by a spectrometer and detecting spectra by a detector (Patent Literature 1).

Recently, needs for microspectroscopes suitable for performing an area analysis over a wide region of a sample are increasing. A mapping measurement (also referred to as a point mapping) which repeats conventional point analysis for each point of a plurality of measurement points of a sample cannot meet the needs sufficiently from the viewpoint of the measurement time due to excess measurement points. If an exposure time per one point is shortened, S/N of the spectrum will be deteriorated. Therefore, the exposure time cannot be shortened.

From the viewpoint of shortening of the measurement time of the area analysis, several mapping measurement techniques have been proposed. Among them, there is a method which irradiates an irradiation light linearly onto a sample and collectively obtains spectra of a plurality of points from the vertically long irradiation region (referred to as a line mapping). In Patent Literature 2, a line mapping that forms a linear irradiation region on a sample by a method of deflecting a beam spot in the Y direction at high speed is disclosed. The irradiation light is irradiated onto the sample in a spot-shape, and when the beam spot is moved in the Y direction by a deflecting unit such as an acousto-optical element, the spot image moves along a slit in an incident slit of a spectrometer. During an exposure period of a CCD detector, the beam spot is moved in the Y direction once or more times so that the sample is linearly irradiated and a plurality of spectra that correspond to a plurality of measurement points in the linear irradiation area is read out during its read-out period. Consequently, within one frame of the CCD detector, a plurality of spectra in the linear irradiation region is obtained collectively. Once imaging of one frame is finished, the sample is shifted in the X direction to repeat the same line irradiation. Such mapping measurement is referred to as a "conventional line mapping" in this context.

In this context, resolution and detection sensitivity defined as follows are used. Spatial resolution is a measurement capability to distinguish two points that are spatially close to each other. Wavelength resolution (also referred to as spectral resolution) is a measurement capability to distinguish two peaks that are close to each other on the spectrum. Detection sensitivity is a ratio of a quantity of the incident light to the detector to a quantity of the irradiation light to the sample. When the quantities of the irradiation light to the sample are the same, the detection sensitivity is higher for those with larger quantity of the incident light to the detector. That is, sufficient quantity of the incident light to the detector may be obtained although the irradiation time to the sample is short.

CITATION LIST

Patent Literature

PATENT LITERATURE 1: Japanese Patent Publication No. JPH9-72848A (FIG. 4)

PATENT LITERATURE 2: Japanese Patent Publication No. JP2007-179002A (FIG. 2)

DISCLOSURE OF THE INVENTION

Problem to be Solved by the Invention

However, even in conventional line mappings, the number of measurement points becomes very large when mapping data with high spatial resolution are to be obtained over a wide region. Further, spectra can be obtained collectively by line irradiation for the Y direction, but the sample needs to be scanned stepwise for the X direction. Thus, the repeated acceleration and deceleration, the setting time and the like of the stage become bottlenecks for shortening the measurement time. Further, when the exposure time per one point is shortened in a high speed measurement, S/N is deteriorated. Thus, necessary exposure time needs to be secured. To control the stage at high speed and accurately, a high performance stage is required. From the reasons mentioned above, it is difficult to shorten the time for a wide range mapping measurement using conventional line mappings.

The present invention has been accomplished in view of the conventional arts, and an object of the present invention is to provide a microspectroscope that can perform spectrometry onto a wide region with high detection sensitivity, at high speed and with high wavelength resolution.

Means to Solve the Problem

To achieve the above-mentioned object, the microspectroscope for a two- or three-dimensional mapping measurement according to the present invention comprises:

a beam shaping unit for shaping an irradiation light into a linear shape;

a movable stage for positioning a sample at a focusing position of the linearly shaped irradiation light;

a focusing lens for focusing a light from a linear irradiation region formed on the sample;

a slit that is provided at an imaging position of the linear irradiation region formed by the focusing lens and is parallel to the longitudinal direction of an image of the linear irradiation region;

a spectroscopic unit for receiving a passing light of the slit and dispersing the image of the linear irradiation region in a direction orthogonal to the longitudinal direction of the image;

a light detection unit for detecting the dispersed image of the linear irradiation region; and a mapping measurement control unit for performing a mapping measurement by synchronizing the movable stage and the light detection unit, wherein the light detection unit is consisted of a light receiving element group arranged in two directions, the longitudinal direction of the image of the linear irradiation region and a dispersing direction which is orthogonal thereto, and the mapping measurement control unit comprises:

a continuous scanning control portion for continuously moving the linear irradiation region in a direction orthogonal to the longitudinal direction of the linear irradiation region by the movement of the movable stage without stopping in the sample;

a light detection control portion for making the light detection unit to perform a light detection cycle that is consisted of an exposure period and a read-out period of the light detection unit during the continuous movement of the linear irradiation region and obtaining one average spectrum of a moving range of the linear irradiation region within one light detection cycle; and a mapping data configuration portion for configuring mapping data by storing the average spectrum per each light detection cycle.

Further, the mapping measurement control unit preferably changes the moving velocity of the movable stage or the cycle period of the light detection cycle so that the moving range during one light detection cycle corresponds to a square having a dimension of the longitudinal direction of the linear irradiation region as one side.

Further, the light detection control portion preferably performs a process for reading out all light-receiving elements collectively that are aligned in a line in the longitudinal direction of the dispersed image of the linear irradiation region in the read-out period.

On the other hand, the mapping measurement control unit preferably changes the moving velocity of the movable stage or the cycle period of the light detection cycle so that the moving range during one light detection cycle corresponds to a rectangle having a dimension of the longitudinal direction of the linear irradiation region as a long side, and the long side corresponds to n-times (n is an integer of two or more) the short side of the rectangle.

Here, the light detection control portion preferably divides all light-receiving elements that are aligned in a line in the longitudinal direction of the dispersed image of the linear irradiation region in n groups and performs the process for collectively reading out the light-receiving elements of each group during the read-out period.

The microspectroscope preferably comprises a switching unit for switching the beam shaping unit to an online and offline position relative to an optical axis of the irradiation light, and when a spot diameter of which the irradiation light having a circular cross section is focused onto the sample without passing through the beam shaping unit is regarded as a focusing limit, the shape of the linear irradiation region formed on the sample through the beam shaping unit has a width dimension corresponding to the focusing limit and a length dimension that is 2 to 500 times the width dimension.

Effect of the Invention

According to such configuration, a spectral image by the linear irradiation is formed on the light detection unit. Thus, a spectral image with high spatial resolution that is comparable to a diffraction limit in a width direction of the linear irradiation light is formed at instantaneous capturing of the spectral image. Further, a light detection with high wavelength resolution can be achieved since the width dimension of the incident slit of the spectroscopic unit can be narrowed. Moreover, the light detection unit is maintained in an exposure state while the linear irradiation light continuously scans the sample, so that a spectral image with high spatial and high wavelength resolution is stored in the light detection unit. That is, an average spectral data of the continuous scanning range based on the spectral image with high spatial and high wavelength resolution can be obtained. Mapping data are constructed on the basis of such average spectra. Accordingly, substantial spatial resolution (the number of measurement points) are deteriorated and the number of read-outs of the light detection unit is decreased. In addition, the measurement time is greatly shortened since stepwise movements such as in conventional line mapping measurements become unnecessary and continuous scanning of a movable table is possible. Further, a necessary exposure time per one point is ensured and the deterioration of S/N can be avoided. As stated above, the microspectroscope of the present invention can perform a mapping measurement over a wide range with high detection sensitivity, high speed and high wavelength resolution.

BRIEF DESCRIPTION OF THE DRAWINGS

FIG. 2 is a diagram illustrating a mapping measurement using the microspectroscope.

FIG. 6 is a diagram showing the relationship between a stage velocity and measurement time in the microspectroscope of the present embodiment.

FIG. 7 is a diagram showing the relationship between the number of measurement points and measurement time of the microspectroscope.

Figure 9:
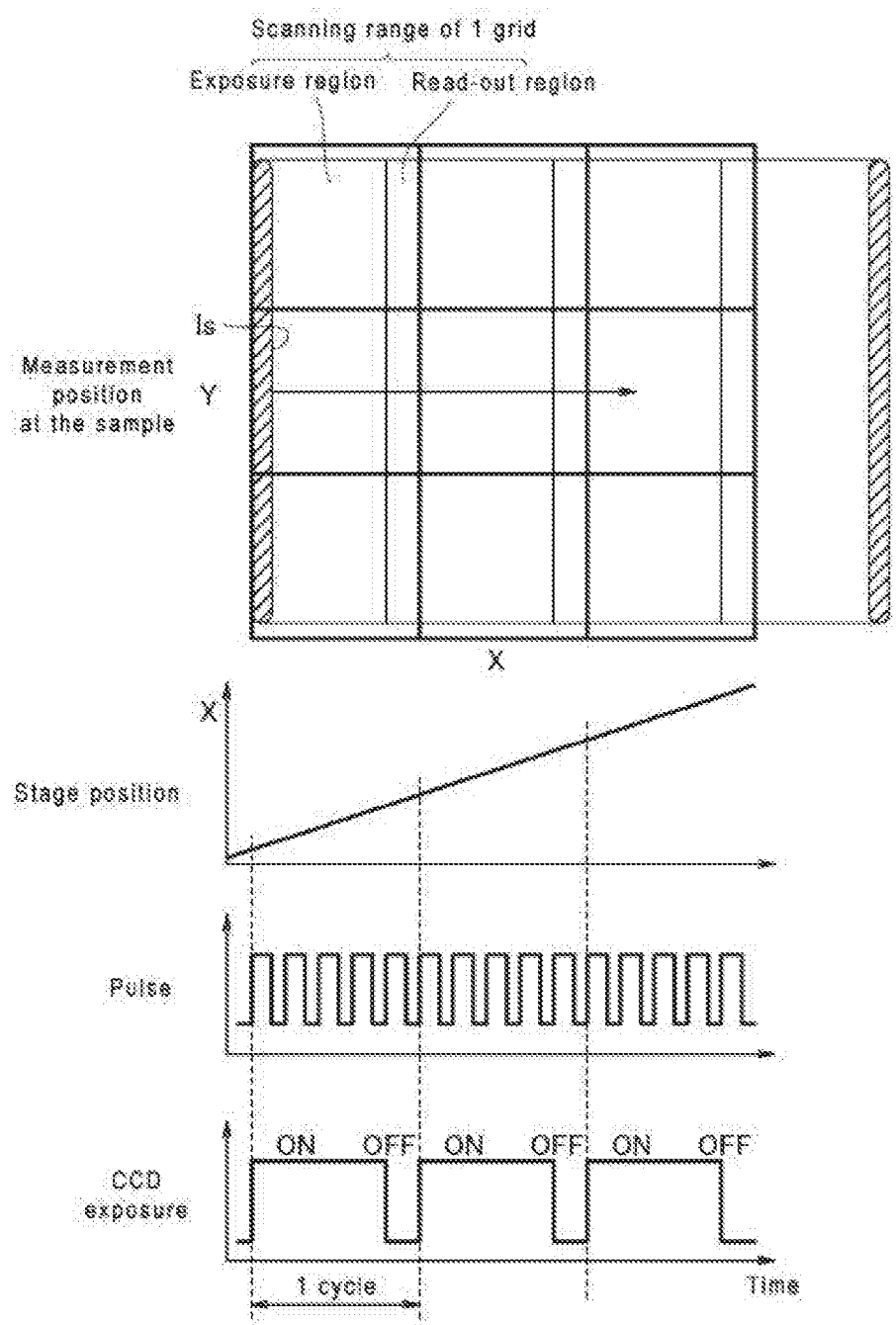

FIG. 9 is a diagram illustrating the mapping measurement using the microspectroscope.

Figure 10:
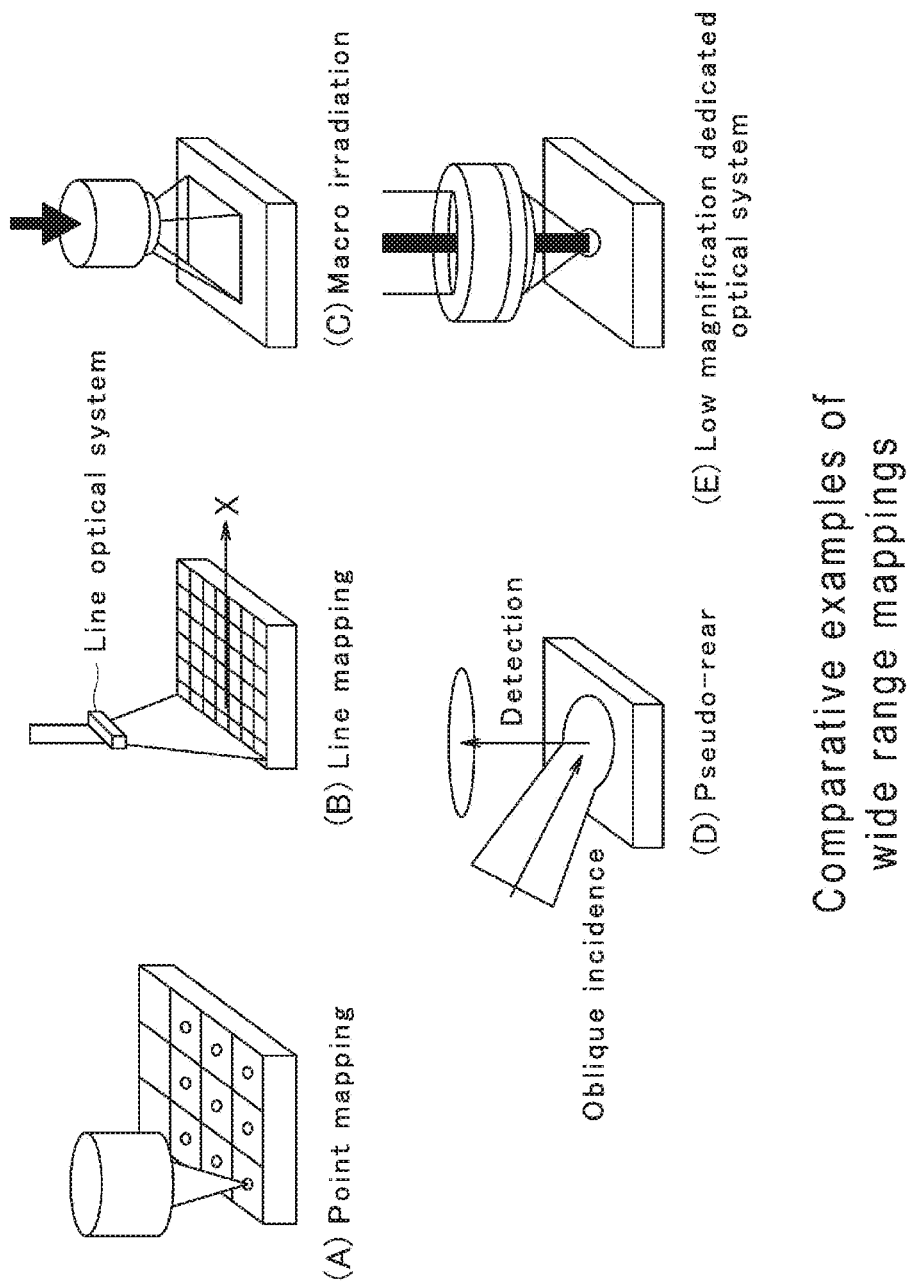

FIG. 10 is a diagram to illustrate comparative examples of wide range mapping measurements. (A) shows a point mapping, (B) shows a line mapping, (C) shows a macro irradiation, (D) shows a pseudo rear irradiation and (E) shows a low magnification dedicated optical system.

Figure 11:
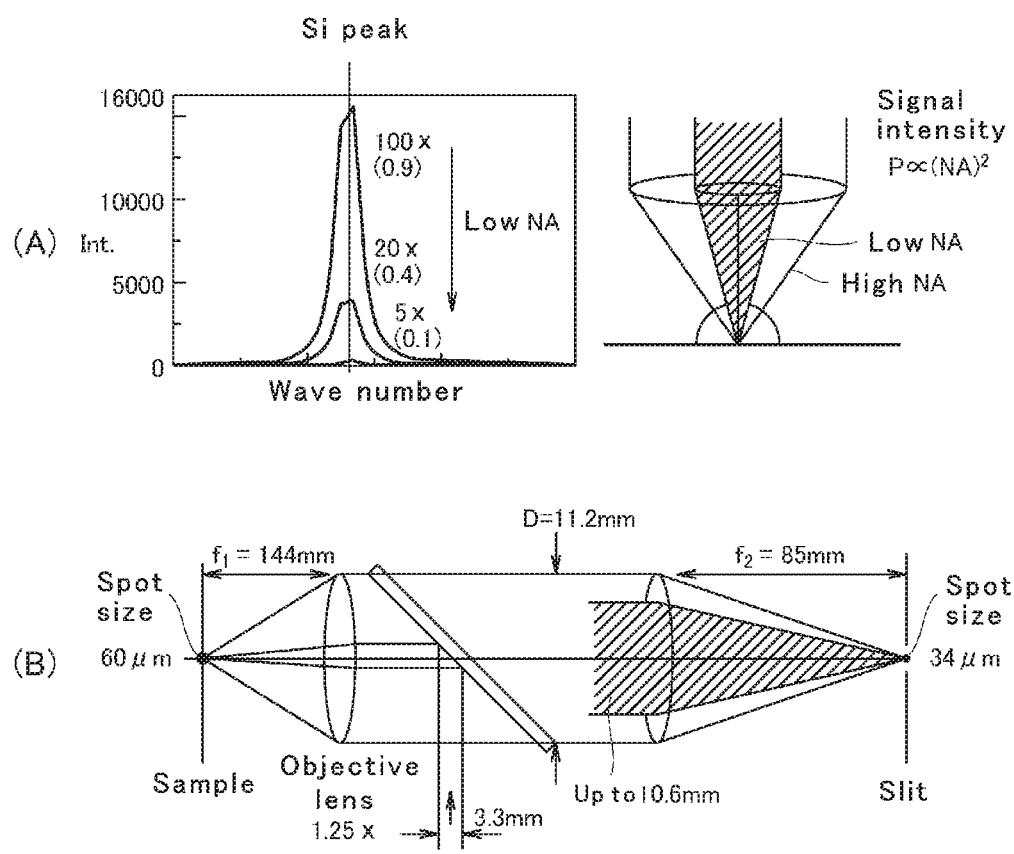

FIG. 11 (A) is a diagram showing the NA and signal intensity of an objective lens. (B) is a diagram to illustrate a comparative example using a low magnification lens.

Figure 12:
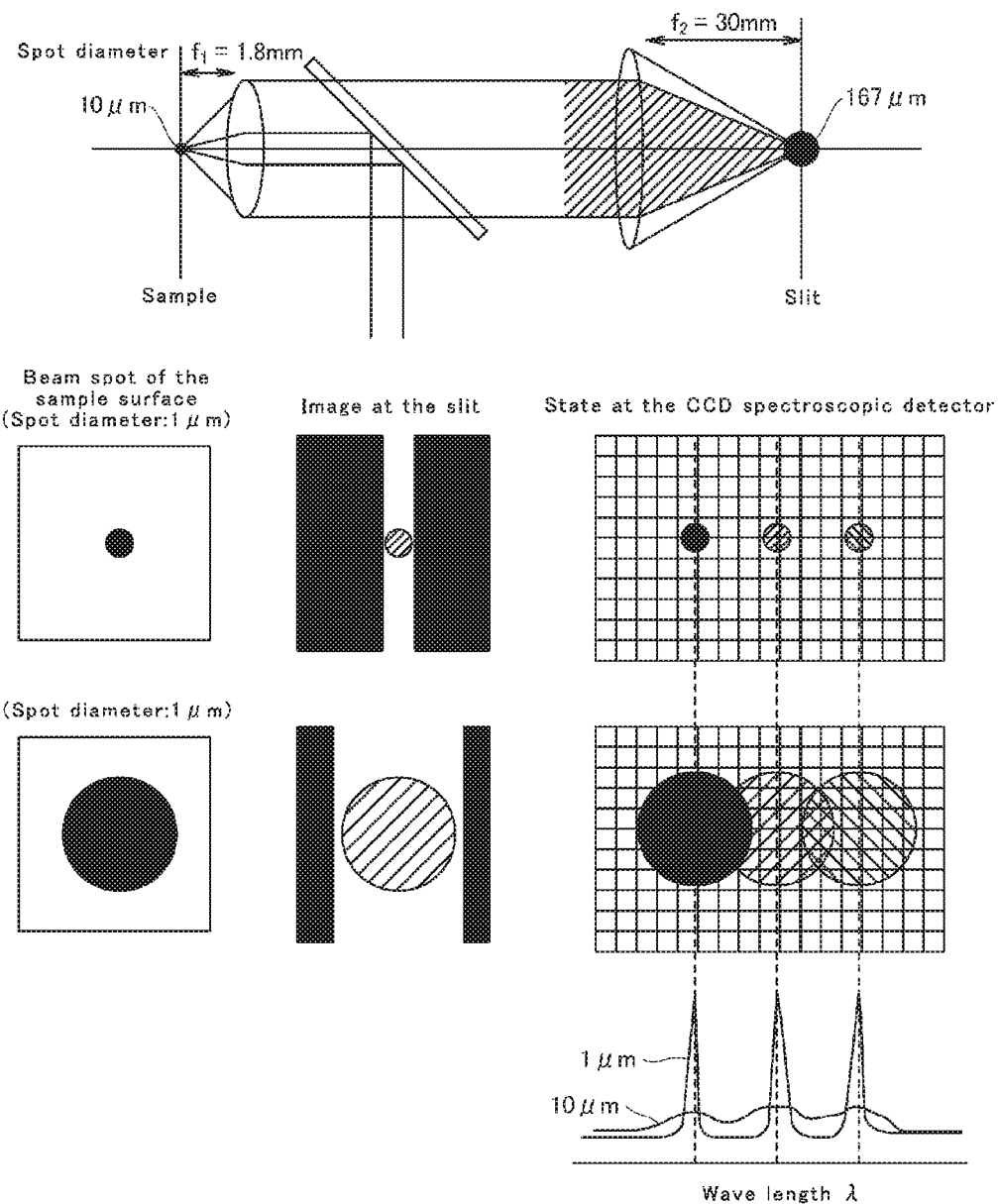

FIG. 12 is a diagram to illustrate a comparative example of a macro irradiation.

DESCRIPTION OF REFERENCE NUMBERS 10, 110 Raman spectroscope (microspectroscope)
26 Cylindrical lens (beam shaping unit)
32 Objective lens (focusing lens)
38 Slit
40 Movable stage
50 Spectrometer (spectroscopic unit)
60 CCD detector (light detection unit)
70, 170 Control device (mapping measurement control unit)
74, 174 Continuous scanning control portion
76, 176 Light detection control portion
78, 178 Mapping data configuration portion

BEST MODE FOR CARRYING OUT THE INVENTION

Figure 1:
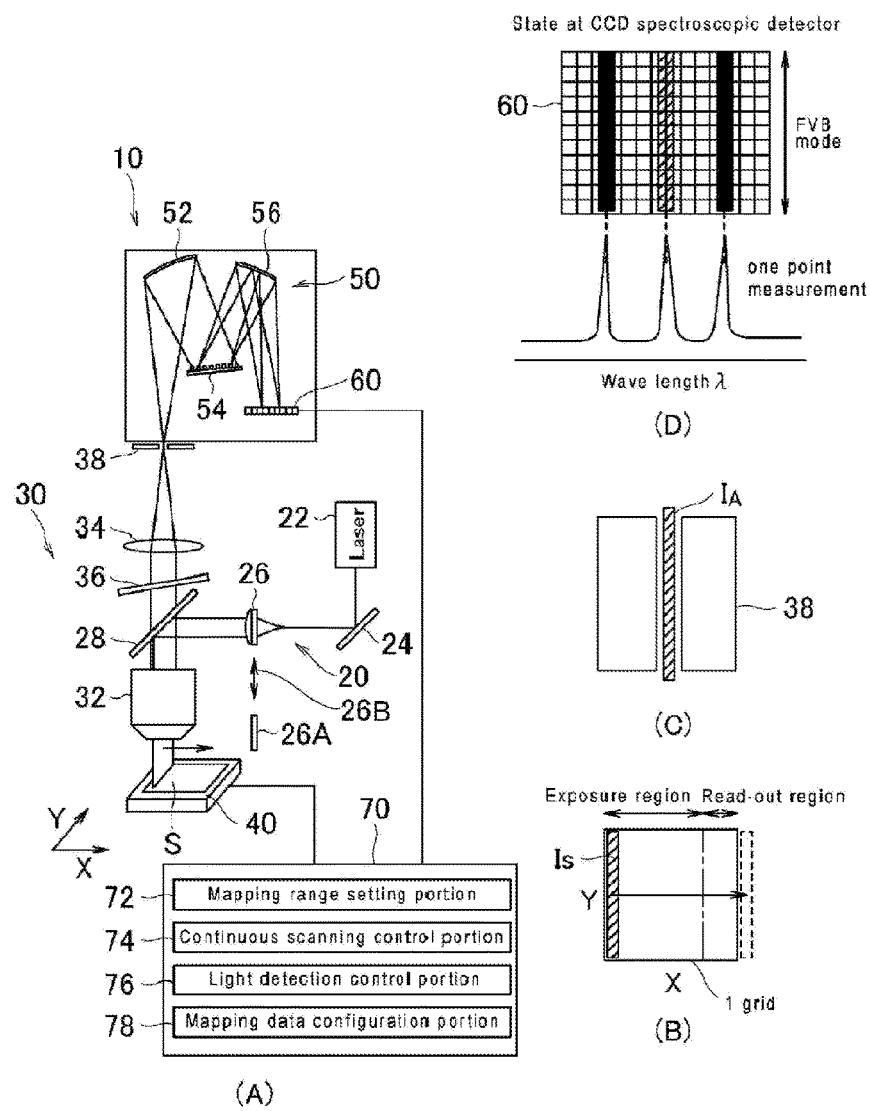
FIG. 1 (A) is a diagram showing an entire configuration of a microspectroscope according to a first embodiment. (B) is a diagram showing an exposure region and a calling region of an irradiation region IS in an exposure period. (C) is a diagram showing the size of an image IA relative to an opening of a slit. A spectral image which the CCD detector receives is shown in (D).

Hereinafter, preferable examples of the present invention are described on the basis of the drawings. FIG. 1 is a schematic view of a microscopic laser Raman spectrophotometer (hereinafter referred to as Raman spectroscope 10), which is a first embodiment of a microspectroscope of the present invention. The Raman spectroscope 10 is a device for spectrally detecting Raman scattered light from a sample S which appears when a laser light is irradiated and thereby obtaining Raman spectrum. In addition, the Raman spectroscope 10 can configure mapping data based on Raman spectra obtained respectively from a plurality of measurement points and is suitable for a two- or three-dimensional wide range mapping measurement. The Raman spectroscope 10 mainly comprises a linear irradiation light source 20 for irradiating a linear beam, a confocal optical unit 30, a movable stage 40, a spectrometer 50, a CCD detector 60, and a control device 70.

First of all, the linear irradiation light source 20 is provided to irradiate a linear irradiation light onto a sample and is consisted of a laser device 22, a mirror 24, a cylindrical lens 26, and a beam splitter 28, for example. The beam splitter 28 is an example of a light flux separation element. The cylindrical lens 26 corresponds to a beam expanding typed beam shaping unit which expands a laser light having a circular cross section and shapes it into a linear irradiation light having an elongated cross section. Further, a laser line generator lens and collimator lens may be used in combination as an alternative of the beam shaping unit.

The linear irradiation light, which is a parallel light, is made incident to the beam splitter 28. The beam splitter 28 reflects the irradiation light towards an objective lens 32 and transmits Raman light from the objective lens 32. The irradiation light forms an elongated linear image, namely, a linear irradiation region $I_S$ on the sample by the combination of the cylindrical lens 26 and the objective lens 32. Here, the cylindrical lens 26 may be set removably from the optical axis of the irradiation system. A switching unit 26B for switching the cylindrical lens 26 to an ordinary beam expanding element 26A may be provided. A beam spot formed by the irradiation light having a circular cross section is formed on the sample when the switched beam expanding element 26A is used. If such switching unit 26B is provided, a smooth shift from the line mapping measurement to the point mapping measurement would be possible.

Alternatively, a beam scanning typed beam shaping unit may be used instead of the beam expanding typed beam shaping unit shown in FIG. 1. In the beam scanning type, an elongated linear irradiation region is formed by making the spot position by the laser light having a circular cross section on the sample move at high speed by using Galvanometer mirror. Either beam shaping unit can form the linear irradiation region $I_S$ that extends in the Y direction, and the Y direction is referred to as the longitudinal direction of the linear irradiation region in this context.

The movable stage 40 is an X-Y biaxial stage having a placing surface parallel to an X-Y plane and can position the sample S on the placing surface to a focusing position of the objective lens 32. When the sample moves back in the X direction (moves in the left direction in the drawing) by the movable stage 40, the linear irradiation region $I_S$ relatively moves forward in the X direction, and thus the sample can be scanned in the X direction. If the movable stage 40 is an X-Y-Z triaxial stage, the sample can be positioned in a depth direction (the Z direction) effectively. If the sample is translucent, a measurement of a foreign substance buried in the sample and the like can be performed. With respect to the Z direction, it is not limited to the triaxial stage, and a dedicated Z axis adjusting device may be provided.

Next, the confocal optical unit 30 is described. The confocal optical unit 30 is consisted of a pair of lenses (the objective lens 32 and the imaging lens 34), a notch filter 36 for cutting Rayleigh light, and a slit 38. The objective lens 32 plays a role of focusing the linear irradiation light from the light source 20 onto the sample S and forming the linear irradiation region $I_S$ as shown in FIG. 1B and a role of focusing Raman light from the irradiation region $I_S$. To make the width of the linear irradiation region $I_S$ narrower and the detection sensitivity higher, it is preferable to use an objective lens having high NA. In the present embodiment, it is distinguished as high NA being 0.4 or more, and low NA being less than 0.4. An objective lens having high NA of 0.4 or more is preferable. As for the upper limit value of NA, when NA is set to 1 or more by using an immersion lens, the acceptance angle of detection will not be 90° or more, and thus the detection sensitivity does not change. The effect of making NA to 1 or more is in the point that the irradiation size can be made smaller.

The imaging lens 34 is arranged on the same optical axis as the objective lens 32. It images the light from the objective lens 32 at a position of the rear slit 38 and forms an image $I_A$ of the linear irradiation region at the position of the slit.

The slit 38 has an opening or a gap having an elongated shape. The longitudinal direction of the opening is parallel to the longitudinal direction of the image $I_A$ of the linear irradiation region. Only the light from the linear irradiation region $I_S$ of the sample passes through the slit 38, and the light from the region outside the linear irradiation region cannot pass through the slit 38. Accordingly, unnecessary light does not enter the spectrometer 50. Therefore, a spectral image formed with high spatial resolution can be formed on the light-receiving surface in the width direction of the linear irradiation region $I_S$ at the moment of continuous scanning. The spectral image which the CCD detector 60 receives is shown in FIG. 1 (D).

Further, the slit 38 is placed at the capturing port of the incident light of the spectrometer 50 and acts as an incident slit of the spectrometer. The narrower the opening of the slit 38 is, the more the wavelength resolution of the spectrometer improves. FIG. 1 (C) is a diagram that illustrates the size of the image $I_A$ relative to the opening of the slit 38.

As the spectrometer 50, a configuration of a general dispersion typed spectrometer is described. The spectrometer 50 is consisted of a front mirror 52 that makes the passing light of the slit into a parallel light flux, a diffraction grating 54 that diffracts the parallel light flux from the front mirror 52, and a rear mirror 56 for imaging the diffraction light from the diffraction grating 54 again in the rear CCD detector 60. The position of the diffraction grating 54 is set so that its diffraction direction shall be a direction orthogonal to the longitudinal direction of the image of the linear irradiation region at the CCD detector 60. Here, the direction which the diffraction direction of the diffraction grating 54 is orthogonal to the longitudinal direction of the image at the CCD detector 60 is the orthogonal direction on the plane that is orthogonal to the optical axis, and it is the horizontal direction if FIG. 1 (D).

The CCD detector 60 is an example of a two-dimensional array typed light detection unit and is consisted of a light-receiving element group arranged in two directions, the longitudinal direction of the image of the linear irradiation region and the diffraction direction orthogonal thereto. In the present invention, the light-receiving element is simply referred to as a pixel.

Since lights of all wavelengths are mixed in the image $I_A$ at the slit 38, Raman light quantity for each wavelength cannot be detected as it is. Whereas, an image (also referred to as a spectral image), of which the imaging position is deviated in the diffraction direction in accordance with the wavelength, is formed by the spectrometer 50 in the CCD detector 60, as shown in FIG. 1 (D). On the light-receiving surface of the CCD detector 60, the diffraction direction of the spectrometer 50 (the horizontal direction in the drawing) is orthogonal to the longitudinal direction of the linear irradiation region (the longitudinal direction in the figure). Accordingly, the area which the diffracted images of each wavelength overlap each other becomes the smallest. As described, a thin slit adapted to the image $I_A$ of the linear irradiation area is used as the slit 38, and thus spectral data with high wavelength resolution can be obtained from the image projected onto the light-receiving surface via the spectrometer 50. For example, a high intensity wavelength light appears as a dark grey band within the diffracted image like the spectral image on the light-receiving surface shown in FIG. 1 (D) and becomes clearly distinguishable from the low intensity wavelength light.

Mapping Measurement Control Device

The control device 70 is for controlling the entire Raman spectroscope, however, in the present embodiment, matters regarding to a mapping measurement using full binning process of the CCD detector 60 is mainly described. To achieve a mapping measurement by a synchronous drive of the movable stage 40 and the CCD detector 60, the control device 70 comprises a mapping range setting portion 72, a continuous scanning control portion 74, a light detection control portion 76, and a mapping data configuration portion 78. The control device 70, for example, may be constructed by Micro Controller Unit (MCU) or a control computer dedicated to the spectroscope. Moreover, the control device 70 has programs for performing each of these functions.

The mapping range setting portion 72 sets a mapping range of the sample S. The mapping range is one which a plurality of grids is aligned two- or three-dimensionally. The grid is square-shaped, and the size (the dimension of one side) represents the spatial resolution of the mapping measurement. The settable size range of one side of the grid vary according to the objective lens, the imaging lens, and/or the CCD detector that are used. For example, a system of which one side of the grid is set to 130 µm is possible by using the 100× objective lens. One side of the grid in the 20× objective lens is its 5 times (650 µm).

As an example, a measurement range (one side of one grid) L of a system, which a 100× objective lens (focal distance $f_1$=1.8 mm), a CCD detector of 200 ch (3.2 mm in length) in the Y direction, and an imaging lens (focal distance $f_2$=85 mm) are combined, is calculated. From the focal distance $f_1$=1.8 mm of the objective lens and $f_2$=85 mm of the imaging lens, the optical magnification M is:

$M$=85 mm/1.8 mm=47.2 times.

Since the size of the CCD detector in the Y direction is 3.2 mm (1 pixel: 16 µm), the measurement range L for the CCD detector to capture the light through the imaging lens and the objective lens is:

$L$=the size of the CCD detector in the $Y$ direction/the optical magnification $M$=3.2 mm/47.2=68 µm.

For example, it is preferable that the objective lens can be switched to objective lenses of 5× ($f_1$=36 mm), 20× ($f_1$=9 mm), 50× ($f_1$=3.6 mm), and 100× ($f_1$=1.8 mm) by a revolver for the objective lenses of a microscope. When the same imaging lens is used, the measurement range (one side of one grid) L of the 5× objective lens is 1355 µm, L=339 µm for the 20× objective lens, L=136 µm for the 50× objective lens, and L=68 µm for the 100× objective lens. Therefore, the target range can be narrowed down smoothly by performing the mapping measurement to a relatively wide range by using the low magnification objective lens at first, and then, gradually switching the objective lenses to those having high magnification. Furthermore, when it is switched to a pin-point measurement from a line macro mapping measurement, the narrowed-down target range can be measured in detail.

In another example, the case when the CCD detector having the size in the Y direction is 6.9 mm (1 pixel: 13.5 µm) is used is similarly calculated. By using the same imaging lens and changing the 5× objective lens to 20×, 50×, and 100×, the measurement range L can be varied from 22 µm to 731 µm, 292 µm, and 146 µm.

In the present embodiment, it is preferable to set the measurement range L to 1 µm to 0.7 mm since it becomes practical from 20× objective lens (NA 0.4) from the viewpoint of sensitivity. When sensitivity is not considered, it is possible to set the measurement range L to 1 µm to 1 mm. In the present embodiment, the measurement range L is set to 100 µm for example, and it is preferable to make the dimension of one side of the grid correspond to the dimension in the longitudinal direction of the linear irradiation region $I_S$. Furthermore, it is preferable to make the region of one grid correspond to a scanning range at one light detection cycle performed by the linear irradiation region $I_S$.

Further, the mapping range setting portion 72 sets the moving velocity of the moving stage 40 and/or the cycle period of the CCD detector according to the size of one grid. That is, the spatial resolution (the size of one grid) of the mapping measurement can be easily adjusted by changing the moving velocity and/or the cycle period. FIG. 1 (B) illustrates only the scanning range for one grid, and the linear irradiation region $I_S$ shown with hatching is the scanning start position.

The continuous scanning control portion 74 makes the movable stage 40 to perform a continuous scanning. The continuous scanning portion 74 can position the sample by the movable stage 40 so that the linear irradiation region $I_S$ is formed at the scanning start position. The continuous scanning is performed by making the movable stage 40 move backwards in the X direction at the set moving velocity. That is, the linear irradiation region $I_S$ continuously moves without stopping in the direction orthogonal to the longitudinal direction of the linear irradiation region $I_S$ (the X direction) by the movement of the movable stage 40.

The light detection control portion 76 controls the light detection of the CCD detector 60 during the continuous movement of the linear irradiation region $I_S$. The light detection cycle of the CCD detector 60 is consisted of an exposure period and a read-out period. The exposure period is a period which the light-receiving elements are maintained in an exposed state, and the read-out period is a period for reading out the received light quantity. The sample S is scanned in the exposed state and is scanned even in the subsequent read-out process of the CCD detector, since the light detection cycle and the continuous scanning are synchronized and performed simultaneously. The scanning of the sample S performed simultaneously without stopping during the light detection cycle of the CCD detector 60 is called the "continuous scanning". It is an expression in comparison to the "step-wise scanning" in conventional line mapping measurements. In FIG. 1 (B), the moving range of the linear irradiation region $I_S$ in the exposure period is shown as an exposure region, and the moving range of the linear irradiation region $I_S$ in the read-out period is shown as a read-out range. The linear irradiation region $I_S$ moves within one grid on the sample, and thus the CCD detector 60 receives Raman spectral image from a different position of the same grid during the exposure period.

Further, in the present embodiment, it is preferable that the CCD detector 60 performs a full binning process in the read-out period. In an ordinary binning process, spectral images are received (exposed) all together by the entire light-receiving surface. Then, several elements are regarded as an element group of one section, and the electric charges of the elements in the section are read out collectively when the exposure is stopped to read out the received light quantity. Particularly, in the full binning process, the received light quantity (electric charge) of all light-receiving elements aligned in a line in the longitudinal direction of the image of the linear irradiation region (the horizontal direction in FIG. 1 (D)) is read out collectively. The total quantity of the received light of one pixel column represents the light intensity of the wavelength in accordance with the position of its pixel column, and one spectral data are obtained by reading out the received light quantity of each pixel column individually. If such full binning process is performed, the frame rate improves because the substantial number of elements which read out electric charges is significantly reduced. Particularly, in the detection of Raman light, which is a weak light, the detection sensitivity is improved by collectively reading out the electric charges stored in a plurality of pixels.

A characteristic point in the present embodiment is that one spectral data read out by the full binning process becomes an average spectral data of the sample within the grid that correspond to one cycle by using the fact that the spectral image which vary in every moment during the exposure period is stored as the electric charge quantity in accordance with the light quantity in the CCD detector 60.

The mapping data configuration portion 78 stores an average spectral data obtained for each light detection cycle and configures mapping data based on the average spectral data.

Measurement Method of the Line Macro Mapping

A mapping measurement method is described by using FIG. 2. The process of the measurement comprises: setting of a mapping measurement S1; positioning of a sample S2; start of the continuous scanning (start of the light detection cycle, simultaneously) S3; repeating operation (restart of row changing and continuous scanning) S4; and construction of the mapping data (mapping display, and the like) S5.

First of all, the mapping range is set onto the sample S by the mapping range setting portion 72. Here, a mapping range consisted of 4 grids of 2 rows by 2 columns (represented as is used for explanation. Subsequently, a measurement program is performed to start the continuous scanning of the movable stage 40 and the light detection cycle by the CCD detector 60. The basic operation of the measurement program consists of: an operation of the movable stage 40 for positioning a scanning start position of the sample S at the focusing position of the objective lens 32; an operation of the laser device 22 for irradiating the irradiation light at the scanning start position; an operation of the movable stage 40 for moving the sample S so that the linear irradiation region $I_S$ continuously moves in a region of one row consisted of a plurality of pixels (2 grids); and an operation of the CCD detector 60 for performing the light detection cycle for the number of grids in one row. When the linear irradiation region $I_S$ reaches a scanning end position, the laser device 22, the movable stage 40, and the CCD detector 60 are stopped.

The operation of the movable stage 40 for continuously scanning the sample S and the operation of the CCD detector 60 for performing the light detection cycle are performed simultaneously. The linear irradiation region $I_S$ continuously scans the sample S from the scanning start position to the last grid of one row without stopping. During this, the CCD detector 60 performs the light detection cycle for the number of grids and sequentially obtains spectral data corresponding to the grids. Further, the measurement program comprises a row-changing operation for aligning the irradiation region $I_S$ to the scanning re-starting position of the adjacent row while kept irradiating after the irradiation region $I_S$ continuously scanned the last grid of one row and an operation for re-starting the continuous scanning. The measurement program is set to repeatedly perform these operations for the number of rows of the grid (for two rows).

The spectral data obtained by the measurement program described above are constructed as mapping data in accordance with the object of spectrometry such as a concentration distribution of compositional components and are displayed on a monitor and the like as necessary. It can be said that each information which constitutes mapping data is an average information of the measurement point within the grid since it is an average spectral data for each grid of the mapping range. According to such measurement method, it is significantly advantageous in the point that a wide range mapping measurement of a sample can be performed at high speed since continuous scanning is performed by the linear irradiation light. Such measurement method is particularly referred to as a "line macro mapping" or "macro mapping".

Figure 3:
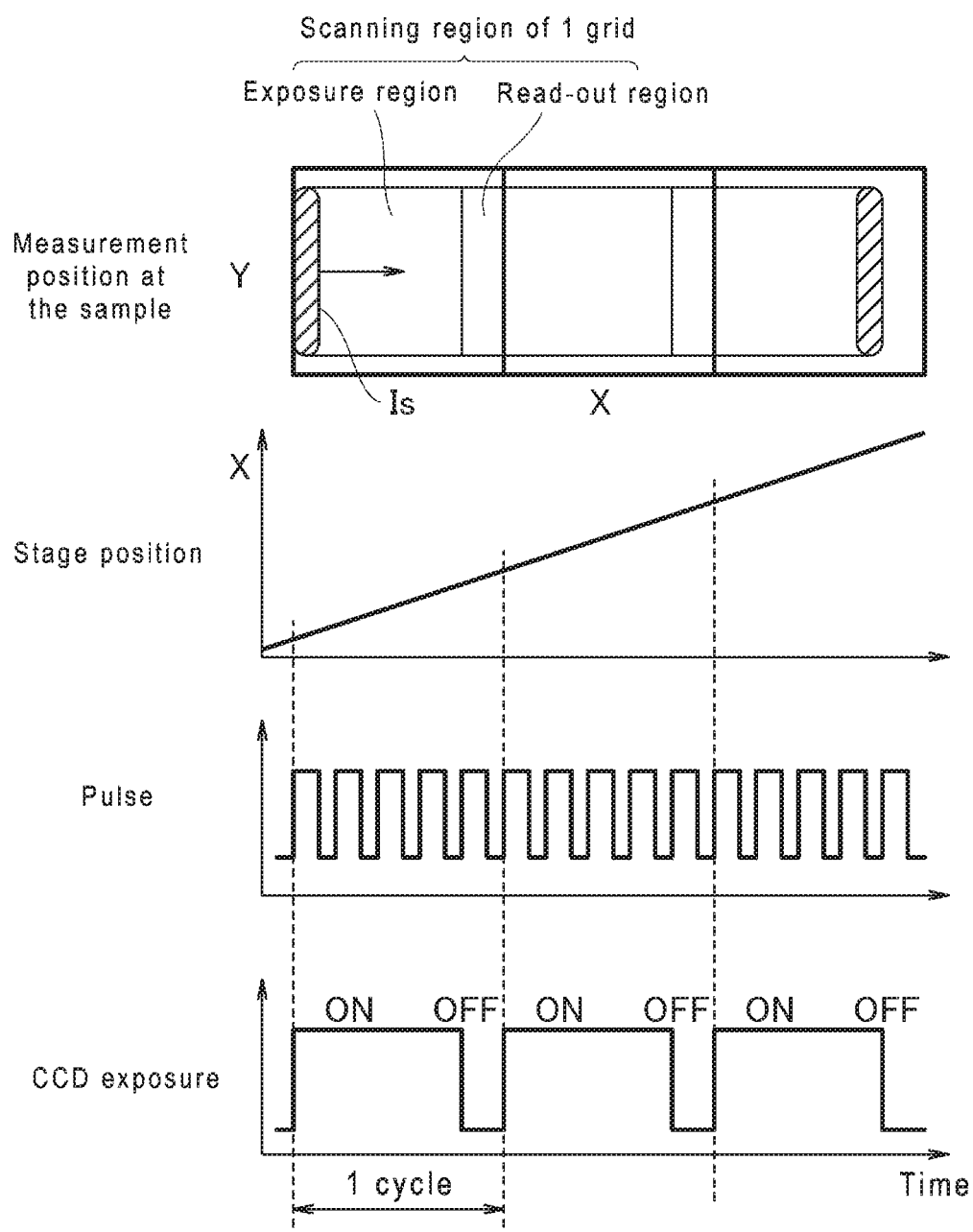
FIG. 3 is a diagram illustrating a synchronizing operation of a movable table and the CCD detector in the microspectroscope.

A method for synchronizing the operations of the movable stage 40 and the CCD detector 60 is described using FIG. 3. FIG. 3 illustrates a time variation of the movable stage 40 and a cycle operation of the CCD detector 60 when the linear irradiation region $I_S$ continuously scans three grids. The movable stage 40 is required to have necessary positioning accuracy and moving velocity, and thus a stepping motor drive type is used, for example. A stepping motor moves the movable stage 40 at a constant speed based on the illustrated pulse signals. Simultaneously, these pulse signals are used for the cycle operation of the CCD detector 60, and the light detection cycle is performed based on count numbers of the pulses. With respect to the exposure operation of the CCD, it exposes in ON period and reads out at full-binning in OFF period. Consequently, each grid can be continuously scanned with high positioning accuracy, and the spectral data synchronized thereto can be obtained.

Difference from the Conventional Line Mappings

Figure 4:
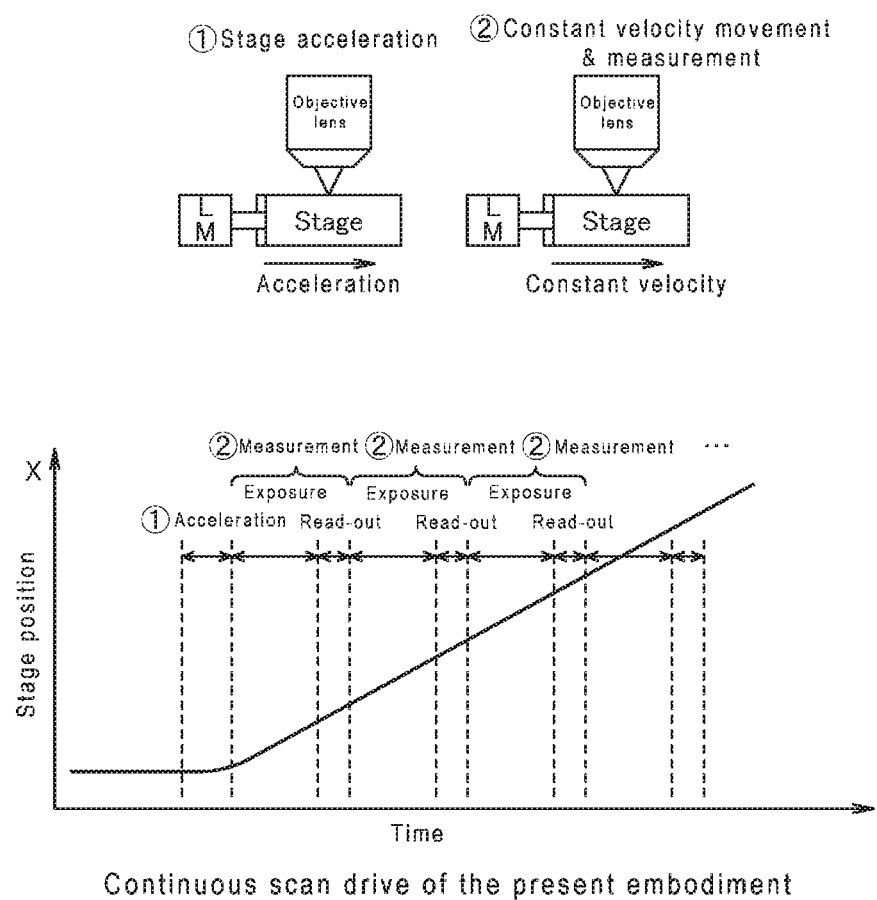
FIG. 4 is a diagram to illustrate an effect of time shortening of the mapping measurement using the microspectroscope.
Figure 5:
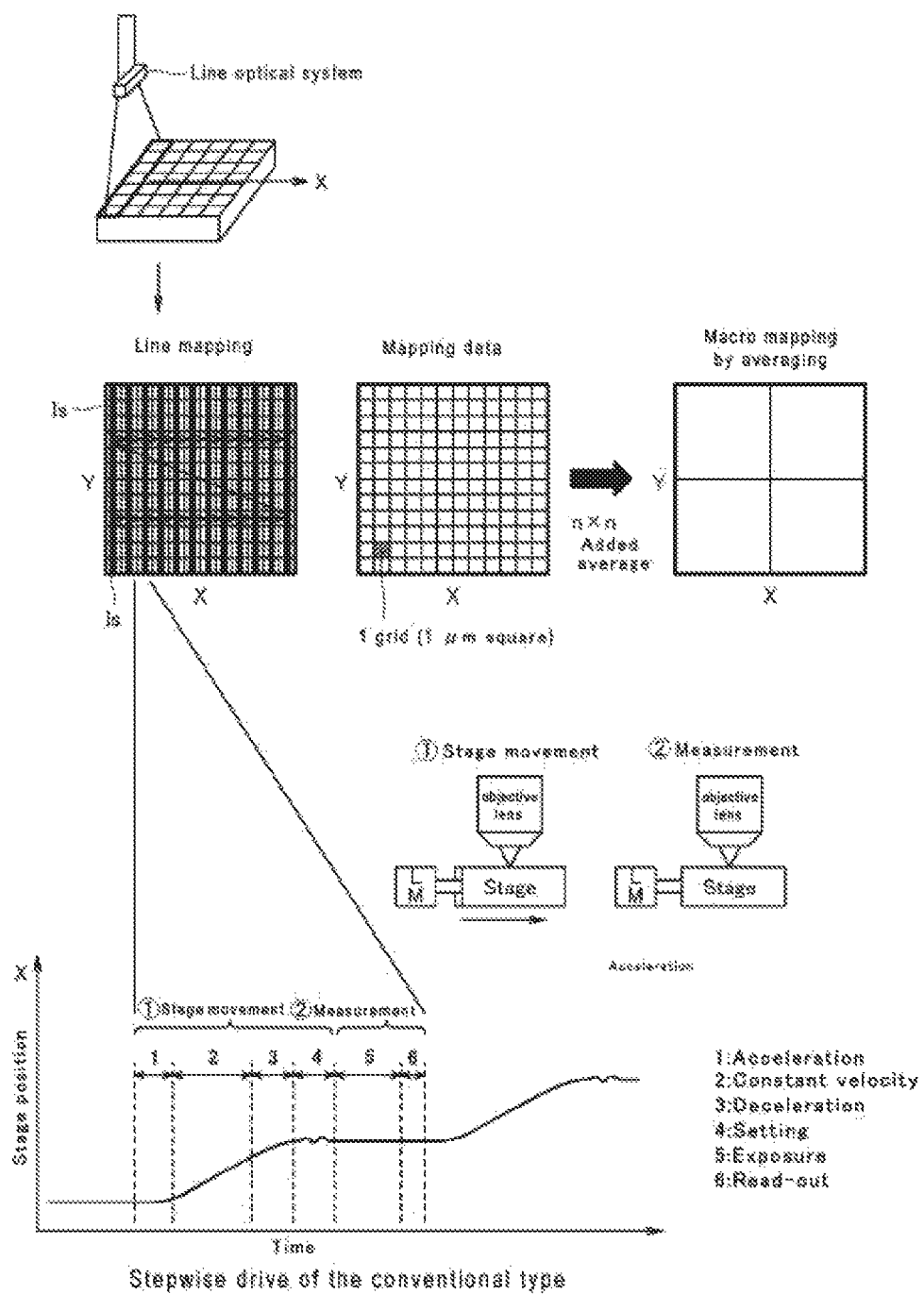
FIG. 5 is a diagram to illustrate the required time for conventional mapping measurements.

A difference from the conventional line mapping is described using FIGS. 4 and 5. In FIG. 4, a synchronizing operation of the movable stage 40 and the CCD detector 60 in the present embodiment is shown together with an acceleration period of the movable stage 40. During acceleration, i.e. until the moving velocity becomes constant, the CCD detector 60 does not start the exposure. When the moving velocity becomes constant, the exposure is started. Once the velocity becomes stable, it maintains the condition and performs the light detection cycle of the exposure and read-out repeatedly. Other operation order is not given to the movable stage 40 until the row-changing operation and the like are required, and the continuous scanning of the movable stage 40 shall not be interrupted.

In FIG. 5, the method of the conventional line mapping is shown. The object of the conventional line mapping is to obtain mapping data with high spatial resolution. Accordingly, the number of spectral data obtained from the mapping range of the same size as the present embodiment is extremely large. The direction which the linear irradiation region $I_S$ is moved is the direction orthogonal to the longitudinal direction of the linear irradiation region $I_S$ (X direction), and the row-changing operation is performed as required. However, to obtain the spectral data with high spatial resolution, the light detection cycle (exposure and read-out) of the CCD detector is performed while the sample is stopped. Accordingly, positioning of the sample by the movable stage has to be performed for the number of grids aligned in the X direction to align the linear irradiation region $I_S$ to the grid column which spectra are desired to be obtained. Since it takes time for the acceleration and deceleration and the setting of the stage, time for one positioning becomes longer. This time differs in accordance with the kinds of the stage. When the positioning of the movable stage is completed, the light detection cycle of the exposure and read-out is started. That is, the exposure is performed while the sample is stopped, and the spectral data from the parts of the sample in accordance with the linear irradiation region $I_S$ are obtained. When the light detection cycle is completed, the sample is positioned again to align the linear irradiation region $I_S$ to the adjacent grid column. Such movements of the stage in steps are referred to as stepwise movements, and the movement and the exposure (including the read-out) is performed alternately. Further, the binning process is not used in the CCD detector, and a fine read-out for each pixel is performed. In the conventional line mapping, mapping data with high spatial resolution can be obtained by such stepwise movement of the movable stage and read-out for each pixel of the CCD detector. For example, when the size of the linear irradiation region $I_S$ of the sample is 1 μm in width and 100 μm in length and the number of pixels of the CCD detector is 100×100 like the present embodiment, the size of one grid for the conventional line mapping is as follows. The region of linear irradiation is positioned in stepwise by 1 μm in the X direction. Then, 100 spectra are obtained in one cycle of the exposure and read-out. Therefore, one side of the grid which obtains one spectrum (spatial resolution) is 1 μm.

The problems of the conventional line mapping is not only that the number of measurement points for obtaining spectral data are excessive, but also that it is difficult to shorten the measurement time since it takes excess time for moving the movable stage for each light detection cycle of the CCD detector. Particularly, setting time until the stage stops after a deceleration period is necessary when the movable stage is stopped, and this leads to the loss of the measurement time, too. Supposing that conventional line mapping is used to obtain macro mapping data, for example, n×n spectral data obtained from n×n grids can be added and averaged to treat them as one spectral data. However, this does not shorten the measurement time because each spectral data are obtained from numerous measurement points. S/N of the CCD detector becomes the value proportional to the square root of n in the added and averaged grid (n×n), but read-out noise at each channel remains.

On the other hand, according to the line macro mapping of the present embodiment, there is no stepwise movement and the measurement time is significantly shortened since the sample is continuously scanned while exposed. Further, in the present embodiment, the number of read-out is significantly reduced since the light detection cycle of the CCD detector is performed only once for the grid of the same size as the grid (n×n) which is added and averaged in the conventional type.

In case of a wide range mapping measurement of 1 mm square to several tens square, there are many cases that high level spatial resolution like the conventional line mapping is not necessary although spatial resolution of obtained mapping data is deteriorated. When compared with the conventional line mapping, the line macro mapping of the present embodiment can be regarded as one which has sacrificed the spatial resolution, but the spatial resolution is enough for a wide range mapping measurement. Furthermore, as described above, macro mapping data can be obtained quickly by the significant shortening of the measurement time.

Further, it is easier to set an exposure time T of one cycle longer than the conventional line mapping. S/N of the CCD detector is proportional to the exposure time T. Accordingly, it is advantageous in the point that S/N can be made higher when the exposure time is extended like in the present embodiment than the added average of the conventional line mapping.

Stage Moving Velocity and Measurement Time

In FIG. 6, an application example of the line macro mapping measurement of the present embodiment is shown.

To measure a component distribution of a tablet, 100 grids are arranged in the X and Y directions respectively in a mapping range of 10 mm square. Each grid has one side of 100 μm. The number of measurement points is 10,000. FIG. 6 is a list showing the scanning velocity of the movable stage 40 and measurement time when the exposure time of one grid (100 μm square) is set in five ways (1, 10, 100, 500 and 1000 ms). The measurement time is calculated as the read-out time and row-changing time of the CCD detector 60 being zero. As the exposure time becomes longer, the measurement time becomes longer. However, in any exposure condition, the measurement times are significantly shortened from the measurement times of the conventional line mapping. As it can be seen from the list, when the exposure time is 1 ms short, the measurement time can be shortened for 10 seconds. However, a movable stage suitable for high speed movement of 100 mm/s will be required. The set lower limit of the exposure time is 10 ms. This is because it takes several ms for reading out in FVB mode. The spectral read-out velocity of an exemplary detector is 269 points in 1 seconds (4 ms per one point), and there are other detectors of 75 points (14 ms), 122 points (8.2 ms), and 396 points (2.5 ms).

In the line macro mapping, a blank region by the CCD read-out is formed when the exposure time is shortened. On the contrary, the blank region becomes smaller when the exposure time is longer. To make S/N higher, the exposure time is desired to be as long as possible. On the other hand, when the exposure time is made longer to 1000 ms, the measurement time becomes 166 minutes. As for the macro mapping of the component distribution of a tablet, the measurement time is desired to be shorter. If the exposure time is set between 10 to 500 ms, S/N, the scanning velocity and the measurement time will be within a practical range. For example, if the exposure time is set to 100 ms, the measurement time will be 17 minutes, and an extremely practical macro mapping measurement can be achieved. It is more preferable to set the exposure time to 50 ms or more.

Further, when the practical range of the exposure time and the measurement time are considered, the performance of the movable stage 40 is enough if it can adapt to the scanning velocity of 1 mm/s, and it is not necessary for the movable stage to adapt to high speed of 10 mm/s or more.

FIG. 7 is a list showing measurement times of when the size of one side of the grid that are aligned in the mapping range is set in 4 ways (1, 5, 10 and 100 μm steps) in the measurement of the component distribution of a tablet like FIG. 6. According to the size of the grid, the number of measurement points becomes one hundred million, four million, one million and ten thousand. Although the longitudinal direction of the linear irradiation region in FIG. 6 is 100 μm, the longitudinal direction of the linear irradiation region is set to 1, 5, 10 and 100 μm in accordance with the size of the grid in FIG. 7. The measurement time becomes longer when the number of measurement points increases, but, in any measurement condition, the measurement time is significantly shortened in comparison to the measurement time of the conventional line mapping measurement. As it can be seen from the list, the measurement times are still too long in 1 μm and 5 μm steps for the macro mapping of the component distribution of a tablet. The condition of measuring one grid in 100 μm step is most practical for a mapping region of 10 mm square.

According to the present embodiment, (1) an average spectral data based on the spectral image with high spatial resolution can be obtained although spatial resolution is deteriorated as mapping data, and mapping data of a wide range can be obtained at high speed (2) with high wavelength resolution and (3) high sensitivity. Hereinbelow, (1) to (3) are described in detail.

(1) An effect of achieving a high speed mapping measurement over a wide range can be obtained by an action of obtaining an average spectral data based on a formation of a spectral image with high spatial resolution. With respect to the width direction (X direction) since a linear irradiation light is used in the present embodiment, a spectral image with high spatial resolution comparable to the diffraction limit of the laser light at capturing of instantaneous Raman spectrum can be formed. Such spectral image is formed on the light-receiving surface of the CCD detector 60, and the CCD detector 60 is maintained in an exposure state while the linear irradiation light scans one grid. Therefore, the linear irradiation region $I_S$ within the grid keeps on moving during the exposure period, and the spectral image with high spatial resolution is stored to the CCD detector 60 at all times. That is, an average spectral data of one grid based on the spectral image with high spatial resolution can be obtained at high speed. Consequently, a high speed mapping measurement over a wide range can be achieved.

(2) An effect of achieving a wavelength resolution of the same level as the conventional line mapping measurement can be obtained. As described above, the present invention uses a linear irradiation light. Therefore, the width dimension of the irradiation region $I_S$ can be shortened to the level corresponding to the diffraction limit of the laser light. Accordingly, the width dimension of the incident slit 38 of the spectrometer can be narrowed. Refer to FIG. 1 (C). Therefore, high wavelength resolution of the same level as the conventional line mapping measurement can be achieved.

(3) An effect of improvement in the detection sensitivity can be obtained. In the present embodiment, Raman light from the linear irradiation region $I_S$ of the sample can be effectively captured since the objective lens 32 having high NA is used. Further, to raise the throughput of the spectrometer 50, an incident optical system which introduces light into the detector needs to be set (F matching) according to the opening angle of the spectrometer. According to the combination of the objective lens 32 having high NA and the incident slit 38 of the present embodiment, F values of the incident optical system and the spectrometer 50 are easy to match without adding a special optical system, and F matching is easy. Therefore, according to the configuration of the present embodiment, high detection sensitivity for weak Raman light can be achieved.

Second Embodiment

Figure 8:
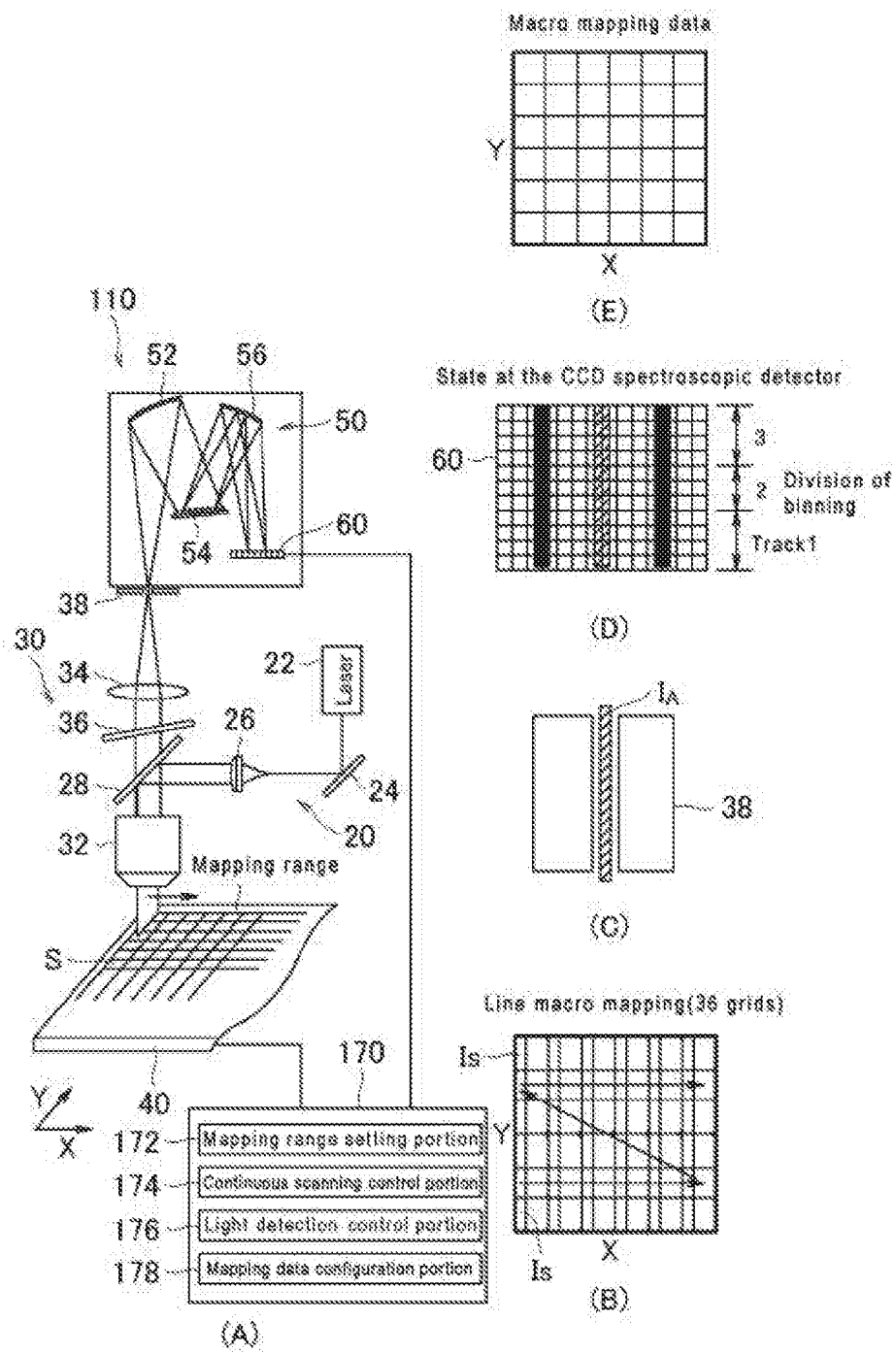
FIG. 8 (A) is a diagram showing an entire configuration of a microspectroscope according to a second embodiment. (B) is a diagram showing a mapping range consisted of 36 grids. (C) is a diagram showing the size of an image IA relative to the opening of the slit. (D) is a diagram showing an ordinary binning process, and mapping data are shown in (E).

FIG. 8 is a schematic view of a Raman spectroscope 110 which is a second embodiment of the microspectroscope of the present invention. The differences from the configuration of the Raman spectroscope 10 of FIG. 1 are a mapping range setting portion 172, continuous scanning control portion 174 and light detection control portion 176 in a control device 170, and other configuration are the same.

The present embodiment is characterized in that the mapping range setting portion 172 sets a grid to a smaller size relative to the dimension of the longitudinal direction of the linear irradiation region $I_S$ and the light detection control portion 176 makes the CCD detector 60 to perform an ordinary binning process.

In FIG. 1, one side of one grid was set to 100 μm, for example. In the present embodiment, the mapping range setting portion 172 sets one side of one grid to (100/n) μm.

Here, n is an integer of 2 or more, and n=3 in FIG. 8. That is, the size of the grid is adjusted to the value which is the dimension of the longitudinal direction of the linear irradiation region $I_S$ divided by n. When the moving velocity of the movable stage 40 is to be maintained, the exposure time at one light detection cycle is shortened since one side of the grid is shorter in this case. When problems of deterioration of S/N occur, the moving velocity of the movable stage 40 is made slower to maintain the exposure period. As described, the grid can be set to a desired size by changing the moving velocity of the movable stage 40 and the cycle period (especially the exposure period) of the light detection. Here, the lower limit of n is 2, but n=1 in the embodiment of FIG. 1. The upper limit of n is described. When the value of which the dimension of the longitudinal direction of the linear irradiation region $I_S$ is divided by n becomes the width dimension of the irradiation region $I_S$, the value is the upper limit of n. For example, when the size of the linear irradiation region $I_S$ is 1 μm in width and 100 μm in length, the upper limit of n value is 100.

In FIG. 8 (B), a mapping range of 36 grids are shown, and the region with hatching is the position of the linear irradiation region $I_S$ at the start of the exposure period of each light detection cycle. The linear irradiation light irradiates the left end part of n grids simultaneously. This means that the moving range of the linear irradiation region $I_S$ at one light detection cycle becomes a rectangle having the dimension of the longitudinal direction of this irradiation region $I_S$ as the long side and the long side becomes a times the short side of the rectangle. The part of the sample on which the linear irradiation region $I_S$ is formed moves within 3 grids simultaneously, and thus the CCD detector 60 receives the spectral image of Raman light from parts of different grids during exposure period. Hence, in the present embodiment, the light detection control part 176 makes the CCD detector 60 to perform the read-out in an ordinary binning process.

As shown in FIG. 8 (D), the ordinary binning process is a process which all light-receiving elements that are aligned in a line in the longitudinal direction (the vertical direction in the drawing) of the image of the diffused linear irradiation region are divided into n groups and the light-receiving quantity (electric charge) of light-receiving elements in each group is read out collectively. That is, the entire light-receiving surface is divided into n tracks, and n spectral data in total are read out for each track. N spectra are the spectra corresponding to n grids that are continuously scanned simultaneously in FIG. 8 (B). As shown, in the present embodiment, n spectral data that are read out in one light detection cycle are the average spectral data within n grids that the irradiation region passes during the cycle.

The mapping measurement method of the present embodiment is basically the same as the measurement method shown in FIG. 1. However, the ordinary binning process is performed at the light detection cycle. Further, in the operation of continuous scanning by the movable stage 40, it was described in FIG. 1 that the linear irradiation region $I_S$ scans the alignment of grids for one row, but in the present embodiment, the linear irradiation region $I_S$ scans the alignment of grids for n rows collectively as shown in FIG. 9. With respect to the exposure control of the CCD detector 60, it exposes in ON period and reads out at binning of n division in OFF period.

According to the configuration of the present embodiment, not only the effect same as the first embodiment can be obtained, but also the size of the grid that obtains spectral data can be easily set to a desired size by changing the moving velocity of the movable stage 40 or the cycle period of the light detection. Therefore, the size of one grid is not limited to the dimension of the longitudinal direction of the linear irradiation, and a mapping range of various numbers of grids can be set even in the same linear irradiation.

Common matters of the two embodiments described above are described. It is preferable to provide a switching unit for switching the beam shaping unit to an on-line and off-line position relative to the optical axis of the irradiation light and irradiate a laser light from the laser device without shaping it into a linear light, if necessary, so that a beam spot can be formed on the sample. Namely, when the spot diameter of when the irradiation light having a circular cross section is focused onto the sample without passing through the beam shaping unit is the focusing limit, it is preferable that the shape of the linear irradiation light $I_S$ that is formed on the sample via the beam shaping unit has a width dimension corresponding to the focusing limit and a length dimension of 2 to 500 times the width dimension. If such switching unit is provided, a point mapping measurement for a necessary weak part can be performed subsequently after the line macro mapping according to the present invention, and a cooperation of the macro measurement and micro measurement can be performed smoothly in one device.

Assuming that a beam spot is imaged on one pixel of the CCD detector by the configuration of the optical system and the adjustment of the spectrometer upon one point irradiation, the maximum settable width of the linear irradiation depends on the size of the CCD detector. The numbers of pixels of exemplary CCD detectors are 200, 255, 400 and 512 channels, and, taking this into consideration, the length dimension of the linear irradiation region $I_S$ is set from 2 times to 500 times of the width dimension.

The present invention is not limited to Raman spectroscopes and is applied to fluorescence spectroscopes and infrared spectroscopes. A laser light is used as the irradiation light in the present embodiment, but an infrared light from high luminance ceramic light source or a halogen lamp are used as the irradiation light in infrared spectroscopes. Further, the present invention is not limited to Raman spectral measurement, and is applied to measurement devices for spectra such as light emissions by a reflected light, a transmitted light and an excitation light of the irradiation light to the sample.

Comparative Example

Hereinbelow, some comparative examples with respect to a wide range mapping are shown, and advantages of the microspectroscope of the present invention are described.

The comparative example of FIG. 10 (A) is a "point mapping method". All area of the mapping range is scanned by a beam spot. Although existing linear stages, EMCCD detectors and multivariate analysis are applied for acceleration, there is a limit for acceleration since there are excessive measurement points, and the exposure time for one point has to be shortened. For detection of a weak light such as Raman light, shortening of the exposure time needs to be avoided due to problems of S/N. For these reasons, the point mapping is not suitable for a wide range mapping.

The comparative example of FIG. 10 (B) is a "conventional line mapping method". Compared to the point mapping, it can be said that spectral data from a plurality of parts along the longitudinal direction of the linear irradiation can be obtained collectively by one cycle of light detection of the CCD detector. However, similar to the description using FIG. 5, the measurement time cannot be sufficiently shortened for the application to a wide range mapping.

Next, a "comparative example using a low magnification objective lens" is described. In the present invention, a high magnification objective lens can be adopted in the same way as the conventional line mapping measurement. The reason why the low magnification objective lens is not preferable is described. In a wide range mapping measurement, the number of measurement points can be reduced if the beam spot on the sample is bigger, and thus the measurement time can be shortened. The smaller the NA (numerical aperture) of the lens is, the bigger the beam spot is. When the low magnification objective lens is used, the beam spot can be made bigger since NA of the lens is small. However, a problem of detection sensitivity (throughput) of the objective lens occurs. It can be said that detection sensitivity is better when the capturing quantity of Raman light by the lens is larger. In a solid substance such as Si substrate of which an entry of light into the sample is less, the signal intensity P of Raman light captured by the objective lens is proportional to the square of NA, and thus the detection sensitivity of the signal intensity will be deteriorated when NA is small. As shown in FIG. 11 (A), when the objective lens of 100× (NA=0.9) is changed to 20× (NA=0.4) and 5× (NA=0.1), the signal intensity decreases to 20% and 1%, respectively. The hatching in FIG. 11 (A) shows the capturing range by a low NA lens. As shown, when the low magnification lens having small NA is adopted, the detection sensitivity of the objective lens will be deteriorated.

In a case which not only the detection sensitivity of the objective lens, but also the F matching of the spectrometer are considered, the reason why the low magnification objective lens is not preferable is described. A low magnification objective lens of 1.25× (MPlanFLN1.25× manufactured by Olympus Corporation. NA=0.04, f1=144 mm) that is mounted to a turret is used. As shown in FIG. 11 (B), when the diameter dimension of the incident parallel light to this objective lens is 3.3 mm, substantial NA is derived as shown below. The pupil diameter D of the lens is D=2·NA·f1=11.5 mm, the substantial NA of the incident side is NAin=NA· (diameter of the incident parallel light)/D=0.011, and the beam spot diameter $\varphi$=1.22·$\lambda$/NAin=about 60 μm. Here, $\lambda$ is the wavelength (0.532 μm) of the incident laser light. In such device condition, an energy loss when the F value of the spectrometer having a focal distance of 20 cm is 8 is investigated. When the focal distance f2 of the imaging lens is 85 mm, the spectrometer can receive the parallel light flux up to 10.6 mm. Energy loss occurs due to the relationship between this and the pupil diameter (11.5 mm) of the objective lens. In a calculation similar to the above-mentioned, when the objective lens of 100× is changed to 1.25× lens, the detection sensitivity of the objective lens is deteriorated to 0.2%. Further, it can be seen that the detection sensitivity is deteriorated even more by the energy loss at the entrance of the spectrometer. When the low magnification objective lens is used, the detection sensitivity is deteriorated. Therefore, it can be seen that a low magnification objective lens should not be easily used for a wide range mapping measurement.

The beam size at the slit position in FIG. 11 (B) is derived as shown below from the relationship to an image magnification M. The image magnification M is M=f2/f1=0.59×. The image size at the slit is (the beam spot diameter $\varphi$)×M=34 μm.

The comparative example of FIGS. 10 (C) and (D) is a "macro irradiation method" and "pseudo-backward irradiation method". As a method to make the beam spot bigger by using high NA objective lens, there are methods of lowering the substantial NA of the incident side as shown in FIG. 10 (C), destroying the parallel light of the incident side, or pseudo-back scattering like FIG. 10 (D). A problem when the beam spot is made bigger by using an objective lens of high NA is described. 100× objective lens (NA=0.9, f1=1.8 mm) and an imaging lens (f2=30 mm) is used. Assuming that a beam spot having a diameter of 10 μm is formed on the sample, the image size at the incident slit of the spectrometer is derived as follows. The image magnification M is M=f2/f1=16.7×. The image size at the incident slit is (the beam spot diameter $\varphi$)×M=167 μm. Hence, the width of the incident slit needs to be made wider. For comparison, an imaging state at the slit width and the CCD detector when the beam spot diameter on the sample is 1 μm is shown. As it is clear from FIG. 12, the spectra obtained in this comparative example have weak peaks and are broad. Therefore, in the method to widen the beam spot by the high magnification objective lens, the wavelength resolution in the CCD detector is deteriorated. Whereas, although high NA objective lens is used in the present invention, it does not make the beam spot on the sample big, but it forms a linear shaped irradiation region by the linear irradiation. Thus, the slit width does not need to be widened, and a measurement with high wavelength resolution is possible.

In the example of pseudo-backward irradiation in FIG. 10 (D), the irradiation area of the irradiation beam is made bigger by oblique incidence. In this case, similarly, wavelength resolution is deteriorated due to the irradiation area being big. Further, the operation distance between the lens and the sample will be smaller when high NA lens is used as the objective lens, and thus oblique incidence will not be possible.

The comparative example of FIG. 10 (E) is a method which uses a "low magnification dedicated optical system". There is a problem of deterioration of the detection sensitivity due to the small NA when a low magnification objective lens is used. To solve this problem, 1× objective lens having a large aperture (NA=0.15) is used. The substantial NA of the incident light is designed so that the beam spot becomes bigger. However, it is difficult to switch the low magnification objective lens to a high magnification objective lens in this method. This is because problems of use of turrets and F matching with the spectrometer occur since the used lens has a large aperture. Therefore, this comparative example will be an optical system dedicated for low magnifications.

As it is clear from the comparative examples listed above, the microspectroscope of the present invention is advantageous from the point of wavelength resolution and detection sensitivity, is suitable for high speed mapping measurement, and also is suitable for switching the magnification of the objective lens.

In the present invention, measurement points refer to a region having a specific area that is a subject for obtaining spectra. Further, squares and rectangles include not only squares and rectangles in a strict meaning but also shapes having rounded angles. Particularly, when the shape of the moving range of the linear beam is a rectangle, a shape which the short side of the rectangle is circular is included.

What is claimed is:

1. A microspectroscope for a two- or three-dimensional mapping measurement comprising:
   a beam shaping unit for shaping an irradiation light into a linear shape;
   a movable stage for positioning a sample at a focusing position of the linearly shaped irradiation light;

a focusing lens for focusing light from a linear irradiation region formed on the sample;

a slit that is provided at an imaging position corresponding to the linear irradiation region formed by the focusing lens and is parallel to the longitudinal direction of an image of the linear irradiation region;

a spectrometer for receiving a passing light of the slit and dispersing the image of the linear irradiation region in a direction orthogonal to the longitudinal direction of the image;

a CCD detector for detecting the dispersed image of the linear irradiation region; and a control computer for performing the mapping measurement by synchronizing the movable stage and the CCD detector, wherein the CCD detector is consisted of a pixel group arranged in two directions, the longitudinal direction of the image of the linear irradiation region and a dispersing direction which is orthogonal thereto, and the control device comprises:

a continuous scanning control program for continuously moving the linear irradiation region in a direction orthogonal to the longitudinal direction of the linear irradiation region by the movement of the movable stage without stopping in the sample;

a light detection control program for making the CCD detector perform a light detection cycle that is consisted of an exposure period and a read-out period of the CCD detector during the continuous movement of the linear irradiation region and obtaining one average spectrum of a moving range of the linear irradiation region during one light detection cycle; and a mapping data configuration program for storing the average spectrum per each light detection cycle and configuring mapping data.

2. A microspectroscope according to claim 1, wherein the control computer changes the moving velocity of the movable stage or the cycle period of the light detection cycle so that the moving range of the linear irradiation region during one light detection cycle moves parallel with respect to the pixel group and corresponds to a square having a length in the longitudinal direction of the linear irradiation region as one side.

3. A microspectroscope according to claim 2, wherein the light detection control program performs a process for reading out all pixels in the pixel group collectively that are aligned in a line in the longitudinal direction of the dispersed image of the linear irradiation region in the read-out period.

4. A microspectroscope according to claim 1, wherein the control computer changes the moving velocity of the movable stage or the cycle period of the light detection cycle so that the moving range of the linear irradiation region during one light detection cycle moves parallel with the pixel group and corresponds to a rectangle having a length in the longitudinal direction of the linear irradiation region as a long side, and the long side corresponds to n-times the short side of the rectangle, wherein n is an integer of two or more.

5. A microspectroscope according to claim 4, wherein the light detection control program divides all pixels in the pixel group that are aligned in a line in the longitudinal direction of the dispersed image of the linear irradiation region in n groups and performs the process for collectively reading out the pixels of each group in the read-out period.

6. A microspectroscope according to claim 1 comprising:
a switch for switching the beam shaping unit to an online and offline position relative to an optical axis of the irradiation light, wherein,
when a spot diameter of which the irradiation light having a circular cross section is focused onto the sample without passing through the beam shaping unit is regarded as a focusing limit, the shape of a linear irradiation region formed on the sample through the beam shaping unit has a width dimension corresponding to the focusing limit and a length dimension that is 2 to 500 times the width dimension.

7. A microspectroscope according to claim 2 comprising:
a switch for switching the beam shaping unit to an online and offline position relative to an optical axis of the irradiation light, wherein,
when a spot diameter of which the irradiation light having a circular cross section is focused onto the sample without passing through the beam shaping unit is regarded as a focusing limit, the shape of a linear irradiation region formed on the sample through the beam shaping unit has a width dimension corresponding to the focusing limit and a length dimension that is 2 to 500 times the width dimension.

8. A microspectroscope according to claim 3 comprising:
a switch for switching the beam shaping unit to an online and offline position relative to an optical axis of the irradiation light, wherein,
when a spot diameter of which the irradiation light having a circular cross section is focused onto the sample without passing through the beam shaping unit is regarded as a focusing limit, the shape of a linear irradiation region formed on the sample through the beam shaping unit has a width dimension corresponding to the focusing limit and a length dimension that is 2 to 500 times the width dimension.

9. A microspectroscope according to claim 4 comprising:
a switch for switching the beam shaping unit to an online and offline position relative to an optical axis of the irradiation light, wherein,
when a spot diameter of which the irradiation light having a circular cross section is focused onto the sample without passing through the beam shaping unit is regarded as a focusing limit, the shape of a linear irradiation region formed on the sample through the beam shaping unit has a width dimension corresponding to the focusing limit and a length dimension that is 2 to 500 times the width dimension.

10. A microspectroscope according to claim 5 comprising:
a switch for switching the beam shaping unit to an online and offline position relative to an optical axis of the irradiation light, wherein,
when a spot diameter of which the irradiation light having a circular cross section is focused onto the sample without passing through the beam shaping unit is regarded as a focusing limit, the shape of a linear irradiation region formed on the sample through the beam shaping unit has a width dimension corresponding to the focusing limit and a length dimension that is 2 to 500 times the width dimension.

* * * * *